United States Patent [19]

Yum et al.

[11] Patent Number: 5,234,424
[45] Date of Patent: Aug. 10, 1993

[54] OSMOTICALLY DRIVEN SYRINGE

[75] Inventors: Su I. Yum, Los Altos; Felix A. Landrau, San Jose; James Z. Huang, Stanford, all of Calif.

[73] Assignee: Alza Corporation, Palo Alto, Calif.

[21] Appl. No.: 691,040

[22] PCT Filed: Dec. 18, 1989

[86] PCT No.: PCT/US89/05669

§ 371 Date: Jun. 25, 1991

§ 102(e) Date: Jun. 25, 1991

Related U.S. Application Data

[63] Continuation-in-part of Ser. No. 290,971, Dec. 28, 1988, Pat. No. 4,969,884.

[51] Int. Cl.$^5$ ............................................. A61K 9/22
[52] U.S. Cl. ................................ 604/892.1; 604/131; 604/151
[58] Field of Search ............... 604/131, 140, 141, 150, 604/151, 218, 235; 424/424–426, 428

[56] References Cited

U.S. PATENT DOCUMENTS

| | | | |
|---|---|---|---|
| 3,604,417 | 9/1971 | Stolzenberg | 604/131 |
| 3,995,632 | 12/1976 | Nakano et al. | 128/260 |
| 4,014,334 | 3/1977 | Theewes et al. | 424/427 |
| 4,410,328 | 10/1983 | Theewes et al. | 604/892 |
| 4,969,884 | 11/1990 | Yum | 604/141 |
| 5,030,216 | 7/1991 | Theeuwes et al. | 604/892.1 |

*Primary Examiner*—C. Fred Rosenbaum
*Assistant Examiner*—Mark Bockelman
*Attorney, Agent, or Firm*—D. Byron Miller; Edward L. Mandell; Steven F. Stone

[57] ABSTRACT

An improved osmotic engine is disclosed. The osmotic engine is adapted to be used with an osmotically driven syringe which can be used to deliver a beneficial agent, such as a drug, at a pre-determined rate over an extended period of time. The osmotic engine has an exterior wall defining a compartment which contains an osmotic solute. The wall comprises a thin permeable and/or microporous material which is permeable to an external fluid such as water but is impermeable to the solute. The wall also has a delivery orifice drilled therethrough. A rigid non-dissolving ring-shaped wall support is provided for maintaining the shape of the engine during use. The wall support also provides an open fluid flow path extending from the semipermeable wall portion toward the delivery orifice. The open fluid flow path minimizes the time required for the engine to begin pumping.

23 Claims, 3 Drawing Sheets

OSMOTICALLY DRIVEN SYRINGE

CROSS-REFERENCE TO RELATED APPLICATION

This application is a continuation-in-part of U.S. patent application Ser. No. 290,971 filed 28 Dec. 1988, now U.S. Pat. No. 4,969,884 issued 13 Nov. 1990.

TECHNICAL FIELD

The invention pertains to a novel and useful osmotically driven syringe and an improved osmotic driver therefor. The syringe delivers a useful agent to an environment of use.

BACKGROUND ART

Over the past decade, much research has been devoted to developing new and useful devices for delivering beneficial agents to agent receptor environments of use. For example, in U.S. Pat. No. 3,760,984 issued to Theeuwes, there is disclosed an osmotic delivery device comprising an inner collapsible container carrying on its outer surface a layer of an osmotic solute and a surrounding layer of a polymer permeable to fluid and impermeable to solute. In U.S. Pat. No. 3,971,376, issued to Wichterle, a device is disclosed comprising a capsule having a unitary wall formed of a substantially noncollapsible elastic material that maintains a constant volume and which is adapted to be implanted subcutaneously. A textile fabric may be imbedded in the capsule wall. The fabric strengthens the wall and acts as a reinforcement. In U.S. Pat. No. 3,987,790 issued to Eckenhoff et al., there is disclosed another osmotic delivery device which contains an outer shape-retaining membrane which is sufficiently rigid to be substantially undeformed by the hydrostatic pressure exerted by water permeating through the membrane.

U.S. Pat. No. 3,995,631 issued to Higuchi et al., discloses a device (FIG. 4) comprising an inner flexible bag containing a drug formulation. The bag separates the drug from an osmotically effective solute material. Both the drug and the solute are contained within a housing having an exterior wall that is, at least in part, semipermeable. U.S. Pat. No. 3,995,632 issued to Nakano et al discloses a similar device which incorporates a movable barrier within the housing. The barrier divides the housing into two compartments, one containing the solute and the other containing the drug. The solute-containing compartment has an exterior wall that is, at least in part, semipermeable. This compartment acts as an osmotic driver for the device. U.S. Pat. No. 4,410,328 issued to Theeuwes discloses an osmotically driven syringe/pump device. The osmotic driver in this device is in the form of a tablet comprising an osmotically effective solute, such as sodium chloride, within a semipermeable wall having a single exit orifice drilled therethrough.

While the above-described devices are useful for delivering many agents, and while they represent a valuable contribution to the delivery art, there has been a need in the art for an osmotically driven syringe/pump utilizing an osmotic driver which can be easily replaced and which can be mounted in an osmotically driven syringe/pump in a fluid tight manner. Unfortunately, the osmotic drivers utilized in the prior art devices have had poor strength and shape-retaining characteristics. These osmotic drivers have typically been in the form of a tablet of an osmotically effective solute (e.g., sodium chloride, lithium chloride, potassium chloride, sodium sulfate, and the like) coated with a thin layer of either a semipermeable or microporous membrane material. Known osmotic drivers were made by compressing the solute into the shape of a tablet and then suspending and tumbling the tablet in a wall-forming composition until a thin membrane wall is formed around the solute. Next, after drying, a passageway is drilled through the wall. The air suspension procedure is described in U.S. Pat. No. 2,799,241; in J. Am. Pharm. Assoc., Vol. 48, pages 451 to 459, 1959; and J. Am. Pharm. Assoc., Vol. 49, pages 82 to 84, 1960. Other wall forming techniques such as pan coating have been used in which materials are deposited by successive spraying of the polymer solution on the solute, accompanied by tumbling in a rotating pan. Generally, the semipermeable wall will be about 0.5 to 50 mils thick.

The semipermeable membrane of the prior art osmotic engines have typically been made from materials such as cellulose acylate, cellulose diacylate, cellulose triacylate, cellulose acetate, cellulose diacetate, cellulose triacetate, and the like. Unfortunately, when these membranes are exposed to water, they tend to soften, weaken and expand due to hydration of the membrane. As the membrane-supporting solute core is dissolved and delivered by the osmotic driver, the driver begins to lose its shape. Once the solute has been completely dispensed, the semipermeable membrane collapses and takes the form of a soft amorphous mass.

U.S. Pat. No. 4,008,719 discloses an osmotic driver having a two-layer semipermeable wall formed of cellulose acetate polymer. Semipermeable walls of this type have a thin dense outer layer and a honeycombed supporting inner layer. The honeycombed layer provides some physical support for the thin outer layer. Unfortunately, the cellulose acetate membranes of the type disclosed in U.S. Pat. No. 4,008,719 possess neither great strength nor rigidity. The membranes typically have a Youngs modulus in the range of only about 1000 to about 5000 psi and a compressive strength at 10% compression of only up to about 100 psi. When the prior art osmotic drivers, having the above-described two-layer membrane wall structure, are hydrated, the membrane wall becomes soft and flexible. Once the driver becomes hydrated and has delivered part or all of its osmotic charge, a compressive pressure of only about 5 psi or less will deform the driver. Accordingly, the prior art osmotic drivers are unable to withstand the compressive stresses imposed by the design and operation of an osmotic syringe/pump according to the present invention.

Therefore, it is an object of the present invention to provide an osmotic driver, adapted for driving a fluid dispensing syringe/pump, and having good strength and good shape-retaining characteristics even after the driver has delivered part or all of its osmotic charge. In particular, it is an object of the present invention to provide an improved osmotic driver having a rigid internal reinforcing structure enabling the osmotic driver to retain its initial shape during use and enabling the driver to withstand the compressive stresses imposed by fixedly securing the driver within an osmotic syringe/pump, all without compromising the operation of the or the syringe/pump.

DISCLOSURE OF THE INVENTION

The present invention provides an improved osmotic engine having a size and shape adapting it to drive an osmotically driven syringe. The osmotic engine includes a shaped wall defining an interior compartment. The interior compartment contains an osmotic solute. At least a portion of the wall is comprised of a material that is permeable to, and hydrated by, an external fluid. The wall material is also sufficiently impermeable to the solute to generate an osmotic pressure differential across the wall after the wall is exposed to an external fluid. The wall also has a passageway therethrough connecting the interior compartment with an exterior environment. The osmotic engine also comprises a rigid non-dissolving wall support for supporting the wall and maintaining the wall shape. The wall support has at least one open fluid flow path extending from the semipermeable wall portion toward the passageway through the wall.

In operation, a solution of the solute is delivered from the engine by external fluid being imbibed through the semipermeable wall portion into the osmotic solute-containing compartment to form a solution containing the osmotic solute. The solution is pumped along the open fluid flow path and through the wall passageway to the exterior environment.

Preferably, the wall support comprises a ring-shaped member comprised of a material selected from rigid plastics, metals, and the like. The wall support material preferably has a Youngs modulus of at least about 50,000 psi and a compressive strength at 10% compression of at least about 20,000 psi. The fluid flow path preferably comprises one or more longitudinally extending grooves in the ring-shaped member.

The present invention also provides an osmotically driven dispensing device for delivering a beneficial agent to an environment of use. The device comprises a syringe having a movable piston, the piston dividing the syringe into a beneficial agent-containing compartment and a driving compartment. The device also contains a fluid reservoir and an osmotic engine intermediate the reservoir and the driving compartment of the syringe.

The osmotic engine includes a shaped wall defining an interior compartment. The interior compartment contains an osmotically effective solute. At least a portion of the wall is comprised of a material that is permeable to and hydrated by an external fluid. The wall material is sufficiently impermeable to the solute to generate an osmotic pressure differential across the wall after the wall is exposed to an external fluid. The wall also has a passageway therethrough connecting the osmotic solute-containing compartment with the driving compartment.

The osmotic engine contains a rigid non-dissolving wall support for supporting the wall and maintaining the wall shape. The support has an open fluid flow path extending from the semipermeable wall portion toward the passageway through the wall. In operation, a beneficial agent is delivered from the device in the following manner. Fluid from the reservoir is imbibed through the semipermeable wall portion into the osmotic solute-containing compartment forming a solution containing the osmotic solute. The solution is pumped along the open fluid flow path and through the wall passageway into the driving compartment. The delivered solution exerts pressure on the piston, forcing the piston to move within the syringe and deliver the beneficial agent from the beneficial agent compartment to the environment of use. Preferably, the wall support in the osmotic engine comprises a ring-shaped member which provides a rigid support for maintaining a fluid-tight mechanical seal between the driving compartment and the reservoir. Preferably the ring-shaped member has a Youngs modulus of at least about 50,000 psi. and a compressive strength at 10% compression of at least about 20,000 psi.

BRIEF DESCRIPTION OF THE DRAWINGS

In the drawings and specification, like parts in related Figures are identified by like numbers.

MODES FOR CARRYING OUT THE INVENTION

Figure 1:
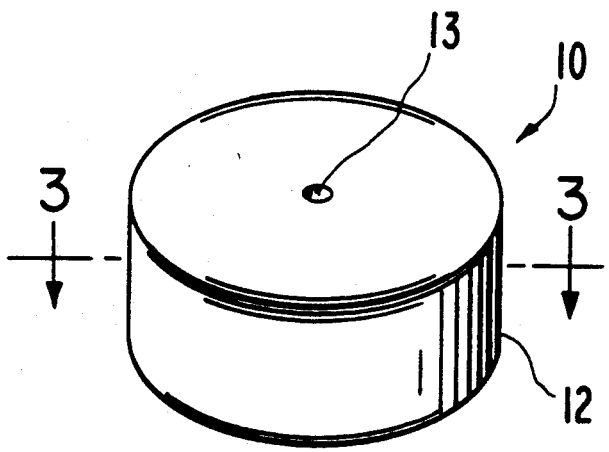
FIG. 1 is a perspective view of the improved osmotic engine of the present invention.
Figure 2:
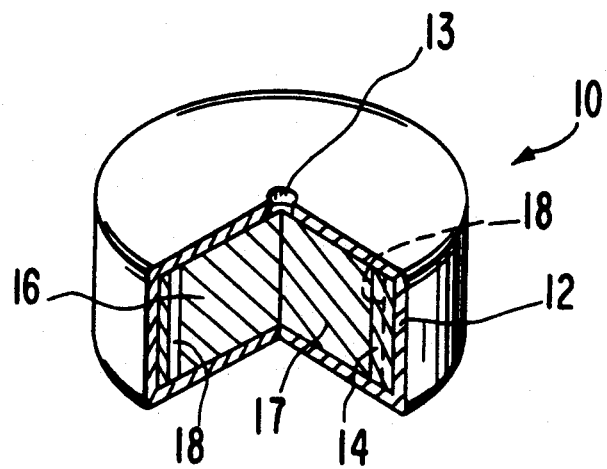
FIG. 2 is an opened view of the osmotic engine of FIG. 1 illustrating the internal structure of the engine.
Figure 3:
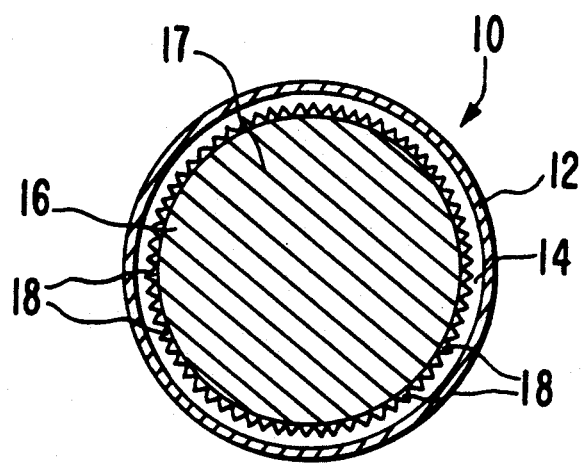
FIG. 3 is a cross sectional view of the engine of FIGS. 1 and 2, taken along line III—III in FIG. 2.
Figure 4:
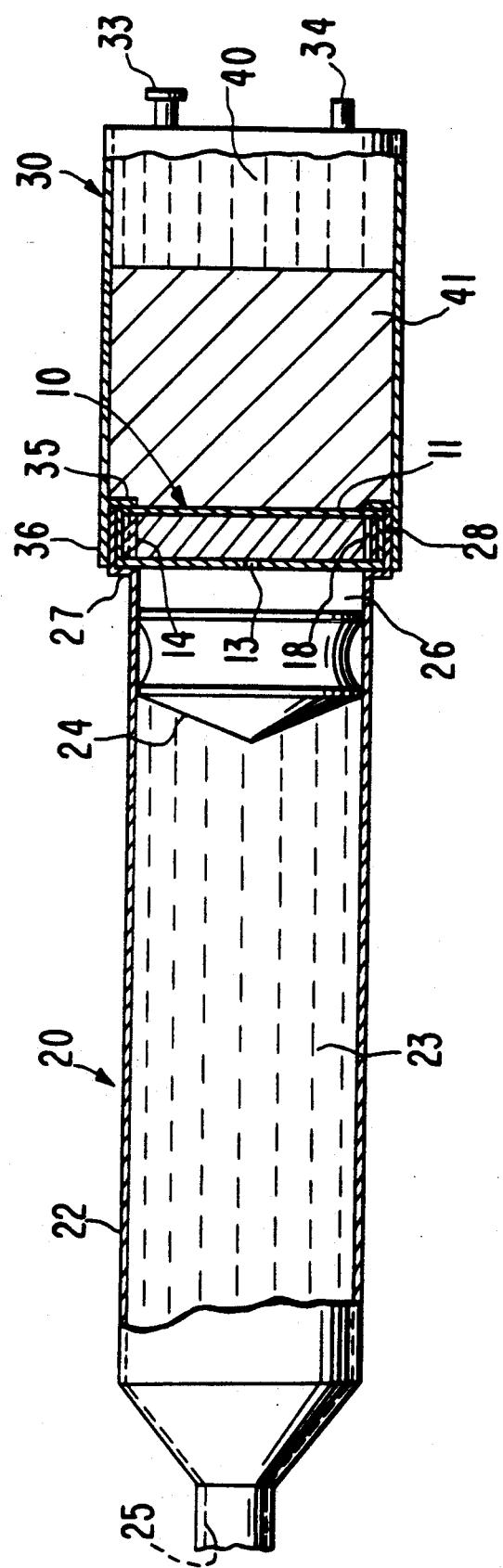
FIG. 4 is a cross sectional view of an osmotically driven syringe utilizing the improved osmotic engine of the present invention.

FIGS. 1-3 of the drawings illustrate one example of an improved osmotic engine and FIG. 4 illustrates one example of a new and useful osmotically driven syringe for dispensing a liquid agent.

The osmotic engine is designated in the Figures by the numeral 10. Osmotic engine 10 comprises a semipermeable or microporous wall that encapsulates both a rigid support ring 14 and a tablet 16 of an osmotic agent represented by 17. A delivery orifice 13 through semipermeable wall 12 provides access to the interior of osmotic engine 10.

The ring 14 is made of a rigid, non-dissolving material such as rigid plastics, ceramics, glasses and/or metals. In order for the osmotic engine 10 to have sufficient strength and rigidity to be used as an osmotic driver in an osmotically driven syringe according to the present invention, the ring 14 should be comprised of a material having sufficient strength and rigidity to withstand the conditions of use in an osmotically driven syringe of the type described herein. Ring 14 is preferably comprised of a material having a Youngs modulus of at least about 50,000 psi and a compressive strength at 10% compression of at least about 20,000 psi. Most preferably, the ring 14 is comprised of an acetyl resin having a Youngs modulus of at least 50,000 psi and a compressive strength (at 10% compression) of at least about 20,000 psi. As best shown in FIG. 3, the inner surface of ring 14 is provided with a plurality of longitudinally extending grooves 18. The ring 14 may be formed, for example, by conventional machining or molding techniques.

The osmotic engine 10 may be formed by pressing a pre-formed tablet 16 of a suitable osmotic agent 17 into the center of ring 14. In this orientation the grooves 18 provide a plurality of open longitudinally extending passageways between ring 14 and tablet 16. The ring 14, with tablet 16 pressed therein, is then coated with a solution of a suitable semipermeable film forming material in accordance with known methods to form the semipermeable/microporous wall 12. Lastly, the orifice 13 is drilled into one side of osmotic engine 10 using a drill, laser or other known technique. The osmotic engine 10 of the present invention may optionally have more than one delivery orifice 13. Furthermore, the size of the delivery orifice(s) 13 is not critical and may be as large as the inner diameter of ring 14.

The osmotic engine 10 operates as follows. The exterior of wall 12 is exposed to a liquid solvent, such as water. The solvent diffuses through semipermeable wall 12 and dissolves the osmotically active agent 17. The osmotic agent solution is then "pumped" out of orifice 13 by fresh incoming liquid solvent permeating through wall Because ring 14 is composed of a rigid non-dissolving material, its structural integrity is not affected by the pumping of solvent and solution through osmotic engine 10. As the active agent 17 within osmotic engine 10 is dissolved, the ring 14 provides a rigid structural support for the semipermeable wall 12. Thus, as the active agent 17 is delivered, the osmotic engine 10 retains its original shape and strength. In the case of a ring 14 composed of an acetyl resin, a compressive pressure of more than 20,000 psi is necessary to collapse the osmotic engine 10, even after substantially all of the active agent 17 has been pumped therefrom.

The longitudinally extending grooves 18 in the ring 14 provide a further advantage over the prior art osmotic engines. Each of the grooves 18 provides an open passageway for conveying the liquid solution pumped through osmotic engine 10. In the prior art devices, the entire volume within the semipermeable walls of the osmotic engine was typically occupied with the osmotically active agent or a combination of active agent and drug. Before these prior art osmotic engines could begin pumping solution, the solvent had to first dissolve enough of the osmotic agent to open a flow path through and/or around the solid osmotic agent. This created an initial delay between the time when the liquid solvent begins to permeate through the membrane of the osmotic engine and the time when the osmotic engine begins pumping solution out of the delivery orifice.

In the improved osmotic engine 10 of the present invention, the delay period is greatly reduced by the open passageways provided by grooves 18. Since the osmotic engine 10 initially contains the open passageways, the incoming solvent need not dissolve a fluid flow path through or around the entire tablet 16 before the solution can reach the orifice 13. Therefore, the time required for osmotic engine 10 to begin pumping solution is greatly shortened.

The prior art osmotic engines having no open fluid flow passageways typically had an initial activation/delay period on the order of about 2 to about 3 hours depending upon the size of the engine. By providing grooves 18 in the osmotic engine 10 of the present invention, the activation/delay period has been reduced by about 2 hours, for equivalently sized engines, thereby providing an activation/delay period of only about 1 hour or less.

Wall 12 of osmotic engine 10 is comprised, in total or at least in part, of a membrane that possesses permeability to an external fluid such as water while simultaneously being essentially impermeable to osmotic agent 17. Wall 12 can be formed of a semipermeable material that has uniform properties across all its dimensions, that is, it is substantially imperforate or substantially homogenous. Alternatively, wall 12 can be formed of a microporous material, that is, a material having micropores or microholes. Furthermore, wall 12 can be formed of a material that is both semipermeable and microporous, allowing an external fluid to permeate through while remaining essentially impermeable to osmotic agent 17. When wall 12 is comprised of a material that is substantially imperforate, molecules of the external fluid dissolve in and diffuse through wall 12 and into engine 10. When wall 12 is comprised of a microporous material, molecules of the external fluid migrate and diffuse into the micropores, then into engine 10. When wall 12 is comprised of a material having both of these properties, external fluid enters engine 10 by a concurrent operation of each of these mechanisms, that is, by osmosis through wall 12 and by diffusion through the pores of wall 12.

Typical materials for forming wall 12 include synthetic or naturally occurring semipermeable and/or microporous membranes known to the art as osmosis and reverse osmosis membranes. Preferably, wall 12 is comprised of a cellulose ester. Examples of suitable membrane materials include commercially available unplasticized cellulose acetate, plasticized cellulose acetate, reinforced cellulose acetate, cellulose nitrate with 11% nitrogen, cellulose diacetate, cellulose triacetate, agar acetate, amylose triacetate, beta glucan acetate, beta glucan triacetate, cellulose acetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate propionate, cellulose acetate p-toluene sulfonate, triacetate of locust gum bean, cellulose acetate with acetylated hydroxyethyl cellulose, hydroxylated ethylene-vinylacetate, cellulose acetate butyrate having a viscosity of from about 10 seconds to about 50 seconds, cellulose acetate butyrate containing about 17 percent of combined butyryl and about 29.5 percent acetyl, cellulose acylate, cellulose diacylate, cellulose triacylate, permselective aromatic nitrogen-containing polymeric membranes that exhibit water permeability and essentially no solute passage, osmosis membranes made from polymeric epoxides, osmosis membranes made from copolymers of an alkylene oxide and alkyl glycidyl ether, semipermeable polyurethanes, semipermeable polyglycolic or polylactic acid and derivatives thereof, thin film membranes as disclosed by Loeb and Sourirajan in U.S. Pat. No. 3,133,132, the membranes of ionically associated polyelectrolytes, the polymers formed by the coprecipitation of polycation and a polyanion as described in U.S. Pat. Nos. 3,276,586; 3,541,005; 3,541,006; 3,546,142; 3,173,876; derivatives of polystyrene such as poly(sodium styrenesulfonate) and poly(vinylbenzyltrimethyl-ammonium chloride), and the like. Generally, membranes having an osmotic fluid permeability of $10^{-5}$ to $10^{-9}$ cm$^3$/atm/hr against a saturated solute solution at the temperature of use while simultaneously possessing a sufficient degree of impermeability to the solute to generate an osmotic pressure differential across the membrane are useful and within the spirit of the invention.

Semipermeable wall 12 may also contain a wall forming pharmaceutically acceptable polymer or agent which acts as a permeability enhancer to aid the passage of fluid into the osmotic engine 10. Representative of polymers and agents for the present purpose include water soluble and/or swellable polymers such as hydroxypropyl cellulose, hydroxypropyl methylcellulose, hydroxyethyl cellulose, ethyl methylcellulose, methylcellulose, acrylics including polyacrylic acid, polyethyl methacrylate, polymethyl methacrylate, pyrrolidones including polyvinyl pyrrolidone, alkylated vinylpyrrolidone polymers, poly(vinylpyrrolidone/vinyl acetate) copolymers, vinylpyrrolidone/dimethylamino-ethylmethacrylate copolymers, maleic acid polymers such as monobutyl ester of poly(methyl vinylether/maleic acid), monoethyl ester of poly(methylvinyl ether/-maleic acid), poly(methylvinylether/maleic anhydride) copolymer, polyvinyl alcohol hydrolyzed 75 to 85%, water soluble agents such as polyethylene glycol, polyethylene oxide, guar gum, gum arabic, dextran, citric acid, triethyl citrate, acetyltriethyl citrate, sucrose, fructose, glycerin, triacetin, and the like.

Various osmotically effective solutes which can be used as the osmotic agent 17 include compounds such as magnesium sulfate, magnesium chloride, sodium chloride, lithium chloride, potassium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid, soluble carbohydrates such as raffinose, glucose, lactose, mixtures thereof and the like. Of these, sodium chloride, potassium chloride, glucose and lactose are preferred. The solid solute can be in any suitable physical form such as particles, crystals, pellets, tablets, strips, film, granules and the like. However, from a manufacturing standpoint, the osmotic agent 17 is preferably first compressed into a solid tablet 16 which can then be easily pressed into ring 14 prior to coating of the ring 14 and tablet 16 with the semipermeable membrane material.

Figure 5:
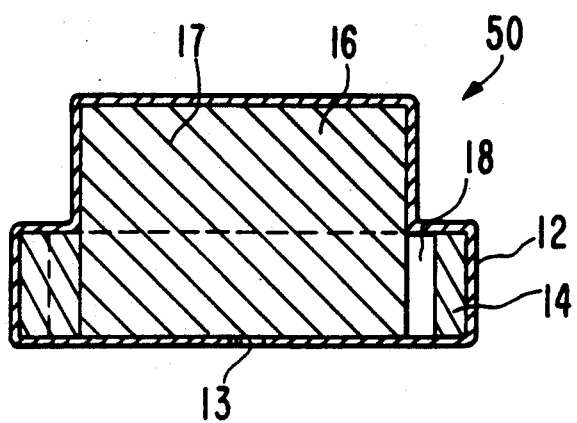
FIG. 5 is a cross sectional view of another embodiment of the osmotic engine of the present invention.

FIG. 5 illustrates an alternative embodiment of an osmotic engine designated by the numeral 50. Osmotic engine 50, like osmotic engine 10 (FIGS. 1-3), comprises a semipermeable or microporous wall 12 that encapsulates both a rigid support ring 14 and a tablet 16 of an osmotic agent 17. A delivery orifice 13 through semipermeable wall 12 provides access to the interior of osmotic engine 50. Unlike osmotic engine 10, tablet 16 in engine 50 has a height which is greater than the height of support ring 14. This results in an osmotic engine having a wall 12 with an expanded surface area for imbibing fluid into engine 50. Thus, engine 50 is able to pump osmotic agent solution out of orifice 13 at a higher rate, since the pumping rate is in part dependent upon the surface area of membrane 12 which can be exposed to a liquid solvent such as water.

In FIG. 4 there is illustrated an osmotically driven syringe 20 in combination with a housing 30 containing a reservoir 40 of liquid solvent. The syringe 20 and housing 30 are sized, shaped and adapted to utilize the improved osmotic engines 10 or 50 of the present invention.

Osmotically driven syringe 20 is made of a wall 22, which surrounds and defines an agent compartment 23 and a driving compartment 26. Syringe 20 has a delivery port 25 which can be shaped to accept a hypodermic needle, an IV catheter or the like. A piston 24 separates the agent compartment 23 from the driving compartment 26. Piston 24 fits snugly against the internal surface of wall 22. Piston 24 may be made of rubber, nylon, polytetrafluoroethylene and the like. Likewise, the components of the osmotically driven syringe may be made from well known materials. The reservoir housing 30 and the syringe 20 may be made from metals or plastics that are inert relative to the liquids they contact and are not irritating to the skin. Examples of such materials are stainless steel, aluminum, polyolefins such as polypropylene and polyethylene, polyesters, polyamides, and polycarbonates.

As illustrated in FIG. 4, compartment 26 contains the osmotic engine 10 which is oriented so that solution is pumped through orifice 13 into compartment 26. Syringe 20 has an annular shoulder 27 providing an enlarged end portion 28. End portion 28 is adapted to be fixedly attached to the end portion 36 of housing 30. In this regard, housing 30 and syringe 20 are provided with suitable fastening means, such as screw threads (not shown in the figure). As shown in FIG. 4, housing 30 is also provided with an annular shoulder 35. When housing 30 is attached to syringe 20, the osmotic engine 10 is tightly compressed between shoulders 27 and 35. Preferably, the shoulders 27 and 35 provide a fluid tight seal with the osmotic engine 10 with the ring 14 compressed tightly between annular shoulders 27 and 35.

Housing 30 preferably contains a wicking material 41 adjacent to the surface 11 of osmotic engine 10 which faces reservoir 40. The wicking material 41 maintains the surface 11 continuously wetted by the liquid solvent in housing 30, regardless of the movement or physical orientation of the syringe and housing assembly.

In operation, the syringe 20 may be filled with a suitable beneficial agent by moving piston 24 with a plunger (not shown), thereby filling compartment 23 with a suitable dose of the beneficial agent. Agents that can be dispensed by syringe 20 include drugs, antibacterials, antifungals, plant growth promoters, surfactants, chemical reactants, and the like. It is within the scope of the present invention to utilize a syringe 20 which has been prefilled with a dose of a liquid beneficial agent or which is filled by the patient using a plunger which can be easily connected to piston 24 for drawing the dosage and which is easily disconnected from piston 24 once the appropriate dosage has been drawn.

Those skilled in the art will of course appreciate that in cases where it is desirable to have the syringe/pump begin immediately dispensing the beneficial agent, the piston 24 is preferably positioned immediately adjacent the osmotic engine 10 in order to minimize the volume of compartment 26 and thereby minimize the time required for the osmotic engine 10 to fill compartment 26 with pumped solution and begin pumping the beneficial agent from compartment 23. Alternatively, compartment 26 may be filled with a liquid before inserting engine 10 in order to minimize engine start-up time.

Next, the osmotic engine 10 is placed within the enlarged end portion 28 of syringe 20. It is important to orient osmotic engine 10 with the delivery orifice 13 facing piston 24. Then, the housing 30 is connected, such as by screwing or snapping, to the enlarged end portion 28, thereby tightly securing the osmotic engine 10, in fluid sealing fashion, between annular shoulders 27 and 35. The rigid annular ring 14 in the osmotic engine 10 should be positioned between the annular shoulders 27 and 35 when the housing 30 is connected to syringe 20. In this way, ring 14 provides a rigid support for the compressive forces exerted on osmotic engine 10 by the annular shoulders 27 and 35.

The thus assembled syringe 20/reservoir 30 is then placed on the skin with a needle (not shown) penetrating the cutaneous layer and lying substantially flush against the skin. Alternatively, the needle can be inserted into a vein and the syringe utilized as an IV infusion device. When the osmotically driven syringe is used in combination with a subcutaneous or IV needle, the needle is preferably composed of stainless steel and has a gauge in the range of 25 to 30.

Alternatively the fluid in compartment 23 may be inert and the syringe may be used simply as a displacement pump. In this alternative the syringe will, of course, have to be suitably interconnected by well known means to a reservoir of a fluid beneficial agent to be discharged, such that the inert fluid displaces the beneficial agent from the reservoir in a predetermined regimen to the desired administration site. Such alternatives are particularly attractive in instances in which the beneficial agent is incompatible with wall 22.

After attaching the housing 30 to syringe 20, a liquid solvent 40 is introduced into housing 30 through port 33. Preferably, the liquid solvent comprises sterile water but other solvents could also be used. Ambient pressure is maintained on the liquid reservoir 40 by means of a vent 34 that extends through the end of housing 30. The vent 34 is filled with a material that is permeable to air but not permeable to the liquid solvent.

The liquid solvent is imbibed through the surface 11 of semipermeable wall 12 into osmotic engine 10 where it forms a solution of the osmotic agent 17. The solution is pumped from the osmotic engine 10 into the compartment 26, quickly filling compartment 26. Thereafter, the pumping of solution from osmotic engine 10 causes piston 24 to move toward delivery port 25, thereby forcing the beneficial agent out of port 25.

The imbibition of solvent from reservoir 40 into engine 10 is caused by an osmotic imbalance between the liquid solvent and the composition of osmotic agent 17. The rate of solvent (e.g., water) influx per unit area of semipermeable membrane will depend upon the composition and thickness of the membrane and the magnitude of the osmotic imbalance (this assumes insignificant back pressure from the piston 24). In syringes that are to be used to administer a drug intravenously, the osmotic pressure of the solute solution must exceed the patient's blood pressure (about 10 kPa). Sodium chloride is an especially effective osmotic solute in that the osmotic pressure of sodium chloride is sufficiently high to remove the dependence of pumping rate on the osmotic pressure of the surrounding environment. By keeping the osmotic imbalance substantially constant, the influx of liquid into osmotic engine 10 will be constant and so will both: (1) the rate of delivery of solution from osmotic engine 10 into compartment 26, and (2) the rate of injection of the beneficial agent from compartment 23. Such operation is called "steady state" or "tonic" operation and is characterized by a controlled constant rate of injection at a predetermined baseline level.

The osmotically driven syringes of the present invention may be used to deliver dosages having a fluid volume in a range of about 0.5 to about 20 cm$^3$ over a period of about 0.5 to about 5 days. The osmotic engines useful in the osmotically driven syringes disclosed herein typically provide a delivery rate of about 0.1 to about 40 cm$^3$/day.

The osmotically driven syringe 20 described herein is particularly useful for the long-term administration of pharmaceutical compositions which can be formulated in liquid form. Specific examples include insulin, analgesics (e.g., morphine sulfate), anti-nausea agents and anti-cancer drugs (e.g., 5-FU).

Syringe 20 can optionally be made as a reusable device. That is, agent compartment 23 can be refilled, osmotic engine 10 can be replaced, with another engine having the same or a different pumping rate, and the reservoir 40 can be refilled.

Figure 6:
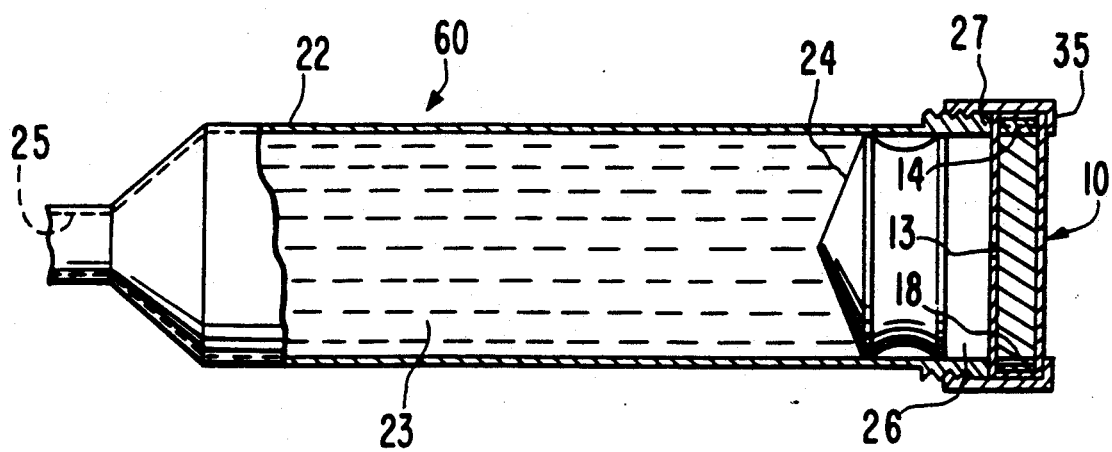
FIG. 6 is a cross sectional view of an osmotically driven syringe adapted for use in an aqueous environment.

In FIG. 6 there is illustrated an osmotically driven syringe 60 which is adapted to be used in an aqueous environment. Unlike syringe 20 (FIG. 4), syringe 60 has no housing containing a reservoir of a liquid solvent. Instead, the osmotic engine 10 is clamped into the end of syringe 60 using suitable fastening means such that osmotic engine 10 is tightly compressed between shoulders 27 and 35. Preferably, the shoulders 27 and 35 provide a fluid tight seal with the osmotic engine 10 with the ring 14 compressed tightly between annular shoulders 27 and 35. In this manner, the bottom surface 11 (e.g., the surface opposite orifice 13) of osmotic engine 10 is exposed to the external aqueous environment.

In operation, the syringe 60 may be loaded using the same procedures described for syringe 20. In order to activate syringe 60, the bottom surface of engine 10 is simply exposed to an environment containing a solvent, preferably an aqueous environment. For example, syringe 60 may be operated by submersing the syringe in water. In a preferred embodiment, syringe 60 is adapted to be implanted in an animal body, whereby aqueous biological fluids activate and drive osmotic engine 10. Implantable pumps may be composed entirely of bioerodible materials such as polylactides, polyglycolides, lactide-glycolide copolymers, and polyorthoesters. In such a case, wall 22, piston 24, and ring 14 are formed of rigid bioerodible materials such as DL-polylactides. In addition, the semipermeable membrane 12 of engine 10 is formed of a semipermeable bioerodible polymer such as a poly(ortho)ester.

While certain preferred embodiments of the present have been selected for illustration in the drawings and have been described in detail herein, the illustrated embodiments should not be construed as limiting and those skilled in the art will appreciate that various modifications, changes and additions to the illustrated embodiments may be made without departing from the spirit and scope of the present invention as defined in the appended claims.

We claim:
1. An osmotic engine comprising:
 (a) a shaped wall defining a compartment, the compartment containing an osmotically effective solute, at least a portion of the wall being comprised of a material that is permeable to and hydrated by an external fluid and having a sufficient degree of impermeability to the solute to generate an osmotic pressure differential across the wall when the wall is exposed to an external fluid, the wall also having passageway therethrough connecting the compartmemt with an exterior environment; and
 (b) a rigid non-dissolving wall support for supporting the wall and maintaining the wall shape, the support having an open fluid flow path extending from the semipermeable wall portion toward the passageway through the wall, the wall support comprising a rig-shaped member and the solute comprising a tablet which fits within the ring-shaped member, the tablet having a height which is greater than the height of the ring-shaped member,
 wherein in operation, a solution of the solute is delivered from the engine by the external fluid being imbibed through the semipermeable wall portion into the osmotic-solute-containing compartment to form a solution containing the osmotic solute, the solution being pumped along the open fluid flow path and through the wall passageway to the exterior environment.
the wall support comprising a ring-shaped member which surrounds the osmotic solute-containing compartment.

2. The osmotic engine of claim 1, wherein the fluid flow path comprises a longitudinally extending groove in the ring-shaped member.

3. The osmotic engine of claim 2 wherein the ring-shaped member contains a plurality of longitudinally extending grooves.

4. The osmotic engine of claim 1, wherein the non-dissolving wall support is comprised of a material selected from the group consisting of rigid plastics, metals, ceramics and glasses.

5. The osmotic engine of claim 6, wherein the wall support material has a Youngs modulus of at least about 50,000 psi.

6. The osmotic engine of claim 4, wherein the wall support material has a compressive strength at 10% compression of at least about 20,000 psi.

7. The osmotic engine of claim 1, wherein the wall is comprised entirely of a material that is permeable to and hydrated by the external fluid.

8. The osmotic engine of claim 1, wherein the semipermeable wall portion comprises a membrane selected from the group consisting of semipermeable and microporous membranes.

9. The osmotic engine of claim 8 wherein the semipermeable membrane is comprised of a cellulose ester and a permeability enhancer.

10. The osmotic engine of claim 1, wherein the external fluid comprises water.

11. The osmotic of claim 1, wherein the osmotically effective solute is selected from the group consisting of sodium chloride, potassium chloride, glucose and lactose.

12. An osmotically driven dispensing device for delivering a beneficial agent to an environment of use, the device comprising:
a) a syringe having a movable piston, the piston dividing the syringe into a beneficial agent compartment and a driving compartment; and
b) an osmotic engine intermediate a sources of fluid and said driving compartment, said osmotic engine including:
(i) a shaped wall defining a compartment, the compartment containing an osmotically effective solute, at least a portion of the wall-being comprised of a material that is permeable to and hydrated by said fluid and having a sufficient degree of impermeability to the solute to generate an osmotic pressure differential across the wall when the wall is exposed to said fluid, the wall also having a passageway therethrough connecting the osmotic solute-containing compartment with the driving compartment;
(ii) a rigid non-dissolving wall support for supporting the wall and maintaining the wall shape, the support having an open fluid flow path extending from the semipermeable wall portion toward the passageway through the wall, the wall support comprising a ring-shaped member and the solute comprising a tablet which fits within the ring-shaped member, the tablet having a height which is greater than the eight of the ring-shaped member;
wherein in operation, a beneficial agent is delivered from the device by said fluid being imbibed through the semipermeable wall portion into the osmotic solute-containing compartment to form a solution containing the osmotic solute, the solution being pumped along the open fluid flow path and through the wall passageway into the driving compartment, thereby exerting pressure on the piston to deliver the beneficial agent from the beneficial agent compartment to the environment of use.

13. The device of claim 12, wherein the fluid flow path comprises a longitudinally extending groove in the ring-shaped member.

14. The device of claim 13, wherein the ring-shaped member contains a plurality of longitudinally extending grooves.

15. The device of claim 12, wherein the non-dissolving wall support is comprised of a material selected from the group consisting of rigid plastics, metals, ceramics and glasses.

16. The device of claim 15; wherein the wall support material has a Youngs modulus of at least about 50,000 psi.

17. The device of claim 15, wherein the wall support material has a compressive strength at 10% compression of at least about 20,000 psi.

18. The device of claim 12; wherein the wall is comprised entirely of a material that is permeable to and hydrated by said fluid.

19. The device of claim 12, wherein the semipermeable wall material is comprised of a cellulose ester and a permeability enhancer.

20. The device of claim 12, wherein said fluid comprises water.

21. The device of claim 12 wherein the osmotically effective solute is selected from the group consisting of sodium chloride, potassium chloride, glucose and lactose.

22. The device of claim 12, including a reservoir of the said fluid.

23. The device of claim 22, wherein the osmotic engine provides a fluid-tight seal between the driving compartment and the fluid reservoir.

* * * * *

UNITED STATES PATENT AND TRADEMARK OFFICE
CERTIFICATE OF CORRECTION

PATENT NO. : 5,234,424
DATED : August 10, 1993
INVENTOR(S) : Su I. Yum, Felix A. Landrau and James Z. Huang It is certified that error appears in the above-identified patent and that said Letters Patent is hereby corrected as shown below:

In claim 1, column 10, line 51, following the word "having" insert --a--; claim 1, column 10, line 59, "rig-shaped" should read --ring-shaped--.

In claim 12, column 11, line 45, "sources" should read --source--; claim 12, column 11, line 50, "wall-being" should read --wall being--; claim 12, column 12, line 11, "eight" should read --height--.

Signed and Sealed this

Twenty-eighth Day of June, 1994

*Attest:*

BRUCE LEHMAN

*Attesting Officer*     Commissioner of Patents and Trademarks